United States Patent
Blackman

(10) Patent No.: US 10,028,991 B2
(45) Date of Patent: Jul. 24, 2018

(54) COMPOSITION, AND METHOD OF USING THE COMPOSITION, EFFECTIVE FOR MINIMIZING THE HARMFUL EFFECTS ASSOCIATED WITH INDIVIDUALS SUFFERING FROM ALCOHOL INTOXICATION

(71) Applicant: GDB Patent Holdings, LLC, Stuart, FL (US)

(72) Inventor: Gregory Blackman, Jensen Beach, FL (US)

(73) Assignee: GDB Patent Holdings, LLC, Stuart, FL (US)

( * ) Notice: Subject to any disclaimer, the term of this patent is extended or adjusted under 35 U.S.C. 154(b) by 0 days.

(21) Appl. No.: 14/933,286

(22) Filed: Nov. 5, 2015

(65) Prior Publication Data

US 2016/0158304 A1 Jun. 9, 2016

Related U.S. Application Data

(63) Continuation of application No. 13/547,757, filed on Jul. 12, 2012, now Pat. No. 9,186,350.

(Continued)

(51) Int. Cl.
| | |
|---|---|
| *A61K 36/752* | (2006.01) |
| *A61K 8/31* | (2006.01) |
| *A61K 31/133* | (2006.01) |
| *A61K 31/137* | (2006.01) |
| *A61K 31/197* | (2006.01) |
| *A61K 31/198* | (2006.01) |
| *A61K 31/352* | (2006.01) |
| *A61K 31/4015* | (2006.01) |
| *A61K 31/4375* | (2006.01) |
| *A61K 31/4415* | (2006.01) |
| *A61K 31/455* | (2006.01) |
| *A61K 31/51* | (2006.01) |
| *A61K 31/519* | (2006.01) |
| *A61K 31/525* | (2006.01) |
| *A61K 31/714* | (2006.01) |
| *A61K 31/732* | (2006.01) |
| *A61K 45/06* | (2006.01) |
| *A61K 36/28* | (2006.01) |
| *A61K 36/73* | (2006.01) |
| *A61K 9/00* | (2006.01) |
| *A61K 9/08* | (2006.01) |
| *A23L 33/15* | (2016.01) |
| *A23L 33/16* | (2016.01) |
| *A23L 33/175* | (2016.01) |
| *A23L 33/21* | (2016.01) |

(Continued)

(52) U.S. Cl.
CPC ............ *A61K 36/752* (2013.01); *A23L 33/15* (2016.08); *A23L 33/16* (2016.08); *A23L 33/175* (2016.08); *A23L 33/21* (2016.08); *A61K 8/31* (2013.01); *A61K 9/0095* (2013.01); *A61K 9/08* (2013.01); *A61K 31/133* (2013.01); *A61K 31/137* (2013.01); *A61K 31/197* (2013.01); *A61K 31/198* (2013.01); *A61K 31/352* (2013.01); *A61K 31/4015* (2013.01); *A61K 31/4375* (2013.01); *A61K 31/4415* (2013.01); *A61K 31/455* (2013.01); *A61K 31/51* (2013.01); *A61K 31/519* (2013.01); *A61K 31/525* (2013.01); *A61K 31/714* (2013.01); *A61K 31/732* (2013.01); *A61K 36/28* (2013.01); *A61K 36/73* (2013.01); *A61K 45/06* (2013.01); *A23V 2002/00* (2013.01); *A61K 8/19* (2013.01); *A61K 8/67* (2013.01); *A61K 8/673* (2013.01)

(58) Field of Classification Search
CPC ...... A61K 36/752; A61K 36/28; A61K 36/73; A61K 8/31; A61K 8/673; A61K 8/67; A61K 8/19; A61K 31/133; A61K 31/137; A61K 31/197; A61K 31/198; A61K 31/352; A61K 31/4015; A61K 31/4415; A61K 31/51; A61K 31/519; A61K 31/525; A61K 31/724; A61K 31/732; A61K 9/0095; A61K 9/08; A23L 33/15; A23L 33/16; A23L 33/175; A23L 33/21; A23V 2002/00

See application file for complete search history.

(56) References Cited

U.S. PATENT DOCUMENTS

| | | |
|---|---|---|
| 6,132,724 A | 10/2000 | Blum |
| 6,245,360 B1 | 6/2001 | Markowitz |

(Continued)

FOREIGN PATENT DOCUMENTS

| | | |
|---|---|---|
| JP | 6014746 | 1/1994 |
| KR | 20020088243 A | 11/2002 |

(Continued)

*Primary Examiner* — Ali Soroush
(74) *Attorney, Agent, or Firm* — The Webb Law Firm

(57) ABSTRACT

The present invention relates to a composition, and methods of using the composition, for minimizing the harmful effects associated with alcohol consumption. The composition includes a plurality of ingredients, which when combined, have the unexpected effect of increasing one or more metabolic pathways in the individual. As the metabolic rate is increased, alcohol is burned off, or utilized as energy source, and occurs at a considerably much faster rate than under normal physiological means. It is believed that the composition may have an effect on the brain causing it to increase metabolic rates. By administering the composition to an inebriated individual, the rate at which a person sobers up, occurs at a faster rate than would occur under normal physiological time frames.

14 Claims, No Drawings

Related U.S. Application Data

(60) Provisional application No. 61/506,732, filed on Jul. 12, 2011.

(51) Int. Cl.
*A61K 8/67* (2006.01)
*A61K 8/19* (2006.01)

(56) References Cited

U.S. PATENT DOCUMENTS

| | | | |
|---|---|---|---|
| 6,340,482 B1 | 1/2002 | Jones | |
| 6,436,946 B1* | 8/2002 | Mann | A61K 31/195 424/752 |
| 6,572,899 B1* | 6/2003 | Gorsek | A61K 31/122 424/725 |
| 6,964,969 B2 | 11/2005 | McCleary | |
| 2004/0077556 A1 | 4/2004 | Chinery | |
| 2005/0025844 A1* | 2/2005 | Boldt | A61K 31/522 424/734 |
| 2005/0181041 A1 | 8/2005 | Goldman | |
| 2005/0271754 A1 | 12/2005 | Cochrane | |
| 2006/0018975 A1* | 1/2006 | Talbott | A61K 31/375 424/646 |
| 2006/0153899 A1 | 7/2006 | Kneller | |
| 2007/0202215 A1 | 8/2007 | Lak | |
| 2009/0068255 A1 | 3/2009 | Yu et al. | |
| 2009/0181922 A1 | 7/2009 | Kneller | |
| 2009/0214628 A1 | 8/2009 | de Rijk | |
| 2010/0081626 A1 | 4/2010 | Owoc | |
| 2010/0239667 A1 | 9/2010 | Hemmingsen et al. | |
| 2011/0008495 A1 | 1/2011 | Paul | |
| 2011/0054038 A1 | 3/2011 | Glozman | |
| 2011/0059882 A1 | 3/2011 | Smith et al. | |

FOREIGN PATENT DOCUMENTS

| | | |
|---|---|---|
| NZ | 530554 * | 4/2004 |
| WO | 2006127605 A2 | 11/2006 |
| WO | 2006127928 A2 | 11/2006 |
| WO | 2007104035 A1 | 9/2007 |
| WO | 2008070368 A3 | 6/2008 |

* cited by examiner

COMPOSITION, AND METHOD OF USING THE COMPOSITION, EFFECTIVE FOR MINIMIZING THE HARMFUL EFFECTS ASSOCIATED WITH INDIVIDUALS SUFFERING FROM ALCOHOL INTOXICATION

CROSS REFERENCE TO RELATED APPLICATIONS

The present invention is a continuation application of U.S. application Ser. No. 13/547,757, filed on Jul. 12, 2012, which will issue on Nov. 17, 2015 as U.S. Pat. No. 9,186, 350, which claims priority under 35 U.S.C. § 119(e) to U.S. Provisional Application 61/506,732, entitled "COMPOSITION, AND METHOD OF USING THE COMPOSITION, EFFECTIVE FOR MINIMIZING THE HARMFUL EFFECTS ASSOCIATED WITH INDIVIDUALS SUFFERING FROM ALCOHOL INTOXICATION" filed on Jul. 12, 2011, the contents of which are herein incorporated in their entirety.

FIELD OF THE INVENTION

The present invention relates to a composition which reduces the levels of alcohol in an individual's system; and more particularly to a composition specifically formulated to increase one or more metabolic pathways resulting in the breakdown of alcohols to sugars in the body, thereby clearing the alcohol from the body at a rate that is faster than normal physiological time periods.

BACKGROUND OF THE INVENTION

Metabolism is a vital aspect of all living organisms. It is the set of chemical reactions which occur within all living organisms in order to maintain life. In humans, metabolism involves complex networks of hormones and enzymes which convert foods into fuel. In general humans receive the energy needed for daily functioning and driving of cellular mechanisms from food sources through metabolism. Specific proteins in the body control the chemical reactions of metabolism, and each chemical reaction is coordinated with other body functions. The process of metabolism involves a continuous balancing of catabolism, the set of processes that break down molecules into smaller units and release energy, and anabolism, the set of processes which build molecules from smaller units.

Alcohol, while prohibited by certain users such as individuals under the age of 21, is commonly used within a variety of beverage types. As a result of its status and ease of manufacture, it is one of the most widely used drugs in the world, acting as a central nervous system depressant. The central nervous system, therefore, is the body system that is most severely affected by alcohol. The drug quickly enters the bloodstream where, depending on the user, it can have numerous effects. Blood alcohol levels are used to legally define if an individual suffers from alcohol intoxication, or is considered "drunk." In most states, the blood alcohol legal limit usually falls between 0.08 and 0.10. The degree to which the central nervous system function is impaired is directly proportional to the concentration of alcohol in the blood.

When ingested, alcohol passes from the stomach into the small intestine, where it is rapidly absorbed into the blood and distributed throughout the body. Because it is distributed so quickly and thoroughly, alcohol can affect the central nervous system even in small concentrations. The American Medical Association has defined the blood alcohol concentration (BAC) level of impairment for all people to be 0.04 grams/100 milliliters of blood (equivalent to 0.04 grains/210 liters of breath). Numerous studies have been undertaken in order to better understand the affects alcohol has on individuals, and how they are commonly expressed. For example, at BAC levels of 0.03 to 0.12, it is not uncommon for individuals to feel euphoria and have one or more symptoms: mild euphoria, become more social and talkative, increased self-confidence, decreased inhibitions, diminution of attention, judgment and control, sensory-motor impairment, and loss of efficiency in finer performance tests. At levels of 0.09-0.25. individuals begin to suffer from emotional instability, loss of critical judgments, impairment of perception, memory and comprehension, deceased sensatory response, increased reaction times, reduced visual acuity, impaired balance, lack of sensory-motor coordination, and drowsiness. At BAC of 0.18-0.3, individuals often become confused, disorientated, have mental confusion, dizziness and exaggerated emotional states, suffer from disturbances in vision and perception, have increased pain thresholds, suffer from apathy, and have slurred speech. At levels of 0.25-0.4, individuals may suffer from near complete loss of motor functions, decreased responses to stimuli, lack of muscular coordination; and impaired consciousness. At levels greater than 0.45, complete unconsciousness and death from respiratory arrest could result.

Once alcohol is consumed, the body handles the drug through the processes of absorption, distribution, and elimination. All three processes generally occur simultaneously. Alcohol is absorbed from the stomach and small intestine by diffusion. Most absorption occurs from the small intestine due to its large surface area and rich blood supply. The rate of absorption varies with the emptying time of the stomach. Generally, the higher the alcohol concentration of the beverage, the faster the rate of absorption. However, above a certain concentration, the rate of absorption may decrease due to the delayed passage of alcohol from the stomach into the small intestine. The maximum absorption rate is obtained with the consumption of an alcoholic beverage containing approximately 20-25% (by volume or v/v) alcohol solution on an empty stomach. The absorption rate may be less when alcohol is consumed with food or when a 40% (v/v) alcohol solution is consumed on an empty stomach. The rate may also slow down when high fluid volume/low alcohol content beverages, such as beer, are consumed. For normal social-type drinking, the highest BAC is usually achieved within 30 minutes after completion of consumption, though it could take as long as 60 minutes. When large amounts of alcohol are consumed over a short time interval, or when a large quantity of food is eaten with the alcohol, the absorption phase may not be complete for up to two (2) hours after last consumption. In other situations, a subject may develop a plateau, where the blood alcohol level does not change for up to two hours. When this occurs, the rate of absorption is equal to the rate of elimination and hence the blood alcohol concentration does not change. After two hours, the rate of elimination will exceed the rate of absorption and the blood alcohol level will begin to decrease. Once in the blood, alcohol is carried throughout the body. The alcohol diffuses into tissues and fluids according to their water content. During the absorption phase, the BAC of arterial blood is greater than the BAC of venous blood. Arteries carry blood to a tissue, and veins remove blood from the tissue. At equilibrium, where the tissue has absorbed a proportionate quantity of alcohol, the BAC of arterial blood is equal to the BAC of venous blood.

Alcohol is eliminated from the body by excretion and metabolism, typically through elimination by the kidney (urine), lung (exhale), or liver where it is chemically broken down to acetic acid. An average person can eliminate 0.5 oz (15 ml) of alcohol per hour. So, it would take approximately one hour to eliminate the alcohol from a 12 oz (355 ml) can of beer. Most alcohol is metabolized, or burned, in a manner similar to food, yielding carbon dioxide and water. A small portion of alcohol is excreted, such as through the breath, leaving the body as alcohol, unchanged. Elimination occurs at a constant rate for a given individual. The median rate of decrease in BAC is considered to be 15 milligrams percent (mg %) per hour. The range of decrease in BAC is 10-20 mg % per hour. This range represents the extreme ends of the rate encountered in a normal population. Most people eliminate at a rate of between 13 and 18 mg % per hour.

Given its effects on individuals, alcohol consumption is commonly undertaken in social situations. Drank responsibly, the body can process the drug accordingly. For the average individual, it is estimated that it takes approximately 4 hours for the body to process and filter 4 ounces of alcohol. The problem associated with alcohol consumption rests in the fact that too much too fast prevents proper possessing and failure to eliminate quickly enough. As increasing levels of alcohol are placed in the body, at some point the body cannot process it fast enough, and high levels circulate within the blood. These high levels affect the brain, resulting in people becoming "drunk." Under the right circumstances, being drunk may not be a problem. However, many individuals who are drunk engage in behavior that often results in unintended consequences. For example, drunken individuals sometimes become very aggressive. This behavior can result in the individual engaging in fights with others, which if sober, would not typically occur. These fights sometimes result in broken bones or bloody lips. However, such actions can result in individuals suffering more severe injuries, such as blunt traumas to the head and/or face, lacerations, or gun shot wounds which may be fatal.

Intoxicated individuals may engage in other risky behaviors, such as driving while intoxicated. As described earlier, drunk individuals often suffer from confusion, decreased motor skills, and inability to properly operate vehicles, resulting in death or serious drunk-driving related injuries. For those individuals who continue to drink extremely large amounts or play various known drinking games which have the affect of consuming large amounts of alcohol, in short times, alcohol poisoning may result. If individuals are not treated properly and/or immediately, death may result.

While there are many home remedies for becoming sober, the most reliable method of reducing inebriation is the passage of time. This allows the body the time to process and clear any alcohol in the individual's system. One of the most difficult parts of treating a person suffering from alcohol poisoning is making the decision to seek medical help. Typically, treatment includes letting the individuals sleep it off. This provides passage of time in order to allow the body to clear the drug from its system. However, in the case where someone is suffering from alcohol poisoning, delay in treatment can be fatal. Treatment for alcohol poisoning typically requires gastric lavage, or stomach pumping, as well as careful monitoring of the individual's respiratory system. Drawbacks to this treatment include the need to get the person to the hospital, the need for invasive medical procedures, and time to allow such actions to counteract the effects of the alcohol.

What is needed in the art, therefore, is a composition, which when taken by individuals suffering from alcohol intoxication, results in the clearance of alcohol from the body at a faster rate than clearance associated under normal physiology. Such a composition, therefore, would have the advantage of reducing negative consequences of intoxicated individuals, such as drunk driving or aggressive behavior, and offer quick relief for those who suffer from the often fatal alcohol poisoning.

DESCRIPTION OF THE PRIOR ART

The instant invention is a unique composition comprising a plurality of ingredients, which have been found to provide unexpected results of reducing the time it takes for an individual suffering from alcohol intoxication to return to a normal, non-inebriated state. The composition includes individually known substances used for other purposes. However, none of the cited references describe a single composition including all of the ingredients for the intended purposes. U.S. Pat. No. 6,245,360 and U.S. Patent Application Publication Number 2007/0202215 describe nutritional supplements which are administered to individuals who are treated for nutritional deficiencies related to alcohol use. Both references describe supplements that comprise mostly a combination of several Vitamin B types as well as other ingredients.

U.S. Pat. No. 6,340,482 discloses materials derived from Citrus plants which can be administered orally to humans for the purpose of producing or maintaining weight loss. In addition, the reference describes using the materials to improve a person's physical performance and increase the person's lean muscle mass. The materials contain at least one of the alkaloids from the group consisting of synephrine, hordenine, octopamine, tyramine and N-methylamine. Two species, *Citrus aurantium* and *Citrus reticulata*, were described as particularly useful. The materials can be administered in their natural form or as extracts, and can be administered in various ways including capsules and tablets. For weight loss and weight control, the materials were described as being administered concurrently with caloric restriction or in the absence of caloric restriction. The description also provides for the materials to be administered for the purpose of increasing muscle mass concurrently with a high protein diet, as well as with an exercise program.

U.S. Publication No. 2006/0153899 and 2009/0181922 describe a dietary supplement comprising palatinose or a derivative thereof. The dietary supplement is described as a nutritional product, a sports performance product, a weight loss product or a meal replacement product. A method of increasing the absorption of a compound into the bloodstream, cells and tissue comprising administering palatinose, or a derivative thereof, in combination with the compound is also described.

United States Patent Application Publication No. 2004/0077556 describes a composition and a method for promoting weight loss in mammals. In addition to promoting weight loss, the composition is described as useful for promoting thermogenesis in mammals, for increasing metabolism and boosting energy levels in mammals, promoting appetite suppression in mammals, for promoting lean muscle mass in mammals and for a diet supplement. The primary mechanism of action is described as increasing norepinephrine levels, which promotes a rise in metabolism, thus leading to more calories being burned and more energy expended primarily through the burning or metabolism of adipose tissue through lipolysis, without the destruction or metabolism of muscle tissue. The nutritional supplement composition comprises of an effective amount of epigallocatechin gallate (EGCG) and other substances which inhibit cyclic adenosine monophosphate (cAMP) phosphodiesterase, stimulate lipolysis, stimulate thermogenesis (i.e., increase metabolism) and/or increase norepinephrine levels, or any combination thereof.

U.S. Publication No. 2010/0081626 discloses an invention which provides formulations and methods for weight loss. The composition described includes a stable aqueous composition with at least one active fat loss agent, particularly, one agent that stimulates a receptor of the beta-adrenergic receptor family and at least one agent that inhibits the alpha-adrenergic family receptor.

U.S. Publication No. 2010/0239667 discloses a layered pharmaceutical composition suitable for oral use in the treatment of diseases where absorption takes place over a large part of the gastrointestinal tract. The composition is described as comprising A, a solid inner layer comprising: i) an active substance, and ii) one or more disintegrants/ exploding agents, one or more effervescent agents or a mixture thereof. The solid inner layer is sandwiched between two outer layers B1 and B2, each outer layer comprising iii) a substantially water soluble and/or crystalline polymer or a mixture of substantially water soluble and/or crystalline polymers, the polymer being a polyglycol in the form of one of a) a homopolymer having a molecular weight of at least about 100,000 daltons, and b) a copolymer having a molecular weight of at least about 2,000 daltons, or a mixture thereof, and iv) an active substance, which is the same as in the solid inner layer A, and layer A being different from layer B. The layered composition is further described as being coated with a coating C that has at least one opening exposing at least one surface of said outer layer, the coating being substantially insoluble in and impermeable to fluids and comprising a polymer, and the composition having a cylindrical form optionally with one or more tapered ends, wherein the ratio between the surface area of one end surface of the cylinder and the length of the cylinder is in a range of from 0.02 to 45 mm.

U.S. Publication No. 2005/0181041 describes a method of preparing mixed phase co-crystals of active agents with one or more materials that allows the modification of the active agent to a new physical/crystal form with unique properties useful for the delivery of the active agent.

U.S. Publication No. 2011/0059882 describes a method for cleaning dentures by contacting the dentures with a solid, multi-layered composition having at least two parts in water. The first part of the composition comprises calcium hypochlorite, magnesium hypochlorite and mixtures thereof, a builder, a water-soluble polymer, and an acid. The first part does not contain sodium hypochlorite, lithium hypochlorite, potassium hypochlorite and mixtures thereof. The second part comprises a functional ingredient and a builder or filler. The second part does not contain any oxidants.

International Publication No. WO2008/070368 describes compositions and methods for diminishing signs of photodamage and/or aging. Certain of the methods are described as comprising contacting skin with an effective amount of one or more elastase enzymes. Certain of the compositions reduce the evidence of elastotic material when contacted with skin. The compositions and methods provide for topical application as well as administration by injection.

U.S. Publication No. 2009/0068255 discloses a system for treating or caring for skin using matrix metalloproteinase (MMP) inhibitors. The system is described as including the use of cosmetic pharmaceuticals which are capable of inhibiting the degradation of proteins found in the skin including collagen, elastin, and other basement membrane and extracellular matrix protein. The MMP inhibitors may be used in both cosmetic compositions and pharmaceutical compositions for application to skin. MMP inhibitors are further described as being formulated with a cosmetically suitable vehicle or pharmaceutically acceptable excipient for application to the skin as creams, lotions, ointments, solutions, or face masks. As for cosmetics, the MMP inhibitor compositions are also described as being capable of preventing or reducing the appearance of wrinkles, pigmentation changes, loss of elasticity, or other effects associated with aging or sun damage. With respect to pharmaceuticals, the MMP inhibitor compositions were also described as applicable to the skin to treat or prevent a skin disease (e.g., proliferative disease, inflammatory disease).

U.S. Publication No. 2009/0214628 discloses compositions and their use for the treatment of human skin, particularly facial skin, to alleviate the symptoms of cosmetic or determatologic skin conditions. The invention describes a composition comprising: one or more metasilicate, one or more carbonate, one or more glyconate, and one or more sulfate. The composition may also contain salts, such as sea slats and other additives or active agents.

SUMMARY OF THE INVENTION

The present invention relates to a composition, and methods of using the composition, for minimizing the harmful effects associated with alcohol consumption. The composition includes a plurality of components, including cognitive enhancers, neurostimulants, metabolic stimulants, mental clarifiers, or mental focusing agents, amino acids, vitamins, electrolytes, minerals, stabilizers, detoxifying agents, metal, toxin, fat absorbing agents, fibers, including dietary fibers, anti-oxidants, and other agents, which when combined, have the unexpected effect of increasing one or more metabolic pathways in the individual. As the metabolic rate is increased, alcohol is burned off, or utilized as an energy source, at a considerably much faster rate than under normal physiological means. It is believed that the composition may have an effect on the brain, causing it to increase metabolic rates. As the brain undergoes such a super-fast metabolic process or directs other metabolic processes to rapidly increase, it utilizes alcohol, which in an inebriated person is plentiful. The alcohol is converted to sugar in order to provide an energy source for the increased metabolism. As a result, alcohol levels in the individual are burned off and removed at a much faster rate than under normal physiological time frames. As the alcohol is burned off, the individual returns to a pre-inebriated state and can function as a normal "non-drunk" individual.

The present invention includes a plurality of components in an effective amount to provide an alcohol based treatment. As used herein, the term "effective amount" generally refers to the amount of a compound that is sufficient to effect treatment as defined herein when administered to an individual, such as a mammal, preferably a human, in need of such treatment. As used herein, the term "treat", "treating" or "treatment" refers to the administration of therapy to a subject, particularly a mammal, more particularly a human, who already manifests or is suspected of manifesting at least one symptom of alcohol inebriation, impairment or poisoning to obtain a desired pharmacological and physiological effect. The term may also include 1) preventing the alcohol intoxication, inebriation, impairment or poisoning, i.e. causing the clinical symptoms and/or characteristics not to develop in a human that may be exposed to or predisposed to the effects of alcohol but does not yet experience or display symptoms of alcohol inebriation, severe or moderate impairment, or poisoning, 2) inhibiting the alcohol intoxication, inebriation, severe or moderate impairment, or poisoning, i.e. arresting or reducing the development of its characteristics or symptoms, including but not limited to sobering up, reducing blood alcohol concentrations, improving cognitive behavior to a level which corresponds to the same level of the individual when not suffering alcohol intoxication, inebriation, severe or moderate impairment, or poisoning, burning off and removing alcohol levels in the blood at a much faster rate than under normal physiological time frames, thus returning the individual to a pre-inebriated state, allowing that individual to function as a normal "non-drunk," or providing for the brain to undergo increased metabolic processes or directing other metabolic processes to rapidly increase and it utilize alcohol in the individual's system as an energy source, or 3) relieving the alcohol intoxication, inebriation, severe or moderate impairment, or poisoning i.e., sobering up, causing regression of characteristics or symptoms including but not limited to reducing blood alcohol concentrations, improving cognitive behavior to a level which corresponds to the same level of the individual when not suffering alcohol intoxication, inebriation, severe or moderate impairment, or poisoning, burning off and removing alcohol levels at a much faster rate than under normal physiological time frames, thus returning the individual to a pre-intoxication or inebriated state, allowing the individual to function as a normal "non-drunk", or providing for the brain to undergo increased metabolic processes or directing other metabolic processes to rapidly increase and it utilize alcohol in the individual's system as an energy source.

Accordingly, it is an objective of the instant invention to provide a composition which, when administered to an individual suffering from alcohol intoxication or alcohol poisoning, results in clearance of any alcohol within the body at a much faster rate than under normal physiological time frames.

It is also an objective of the instant invention to provide a composition which, when administered to an individual suffering from alcohol intoxication or alcohol poisoning, results in increasing one or more metabolic pathways that converts the alcohol to sugars as a source of energy.

It is a further objective of the instant invention to provide a composition which acts as a neurostimulant acting on the brain to increase metabolic pathways, converting alcohol to sugar.

It is a further objective of the instant invention to provide a composition which reduces the time it takes for an alcohol intoxicated individual to become sober.

It is yet another objective of the instant invention to provide a composition which reduces the time it takes to remove alcohol from an individual who suffers from alcohol poisoning.

It is a still further objective of the invention to provide a composition which reduces the time it takes the body of an individual who suffers from alcohol intoxication to remove the alcohol from a period measured in hours to a period measured in minutes.

It is a further objective of the instant invention to provide a composition which reduces the time it takes the body of an individual person who suffers from alcohol intoxication to reduce levels alcohol to less than the legal limit within less than 30 minutes.

It is a further objective of the instant invention to provide a composition which reduces the time it takes the body of an individual person who suffers from alcohol intoxication to reduce the amount of alcohol levels in a time period of around 15 minutes.

Other objectives and advantages of this invention will become apparent from the following description.

DETAILED DESCRIPTION OF THE INVENTION

In certain embodiments of the present invention, a plurality of ingredients is combined to form a unique composition. Administering the composition to an individual who is intoxicated or otherwise contains high levels of alcohol in their blood results in increasing the rate of one or more metabolic pathways, thereby decreasing the amount of alcohol in the blood as the metabolic processes use the alcohol as a source of energy. Administration of the composition, therefore, results in breakdown of the alcohol, as well as a removal or reduction of the feeling of inebriation, at a much faster rate than accomplished under normal physiological time frames.

In certain embodiments, the composition comprises bitter orange. Bitter orange refers to a citrus tree, *Citrus aurantium*, and its fruit. Although native to east Africa and tropical parts of Asia, *Citrus aurantium* is now grown in the Mediterranean regions and parts of the United States. It is also known as Seville orange, sour orange, Zhi shi, and marmalade orange. Bitter orange is used in a variety of applications including foods, cosmetics, essential oils for perfumes, and aromatherapy products. Bitter orange has been used in traditional Chinese medicine and by indigenous people of the Amazon rainforest for nausea, indigestion, and constipation. The extract of bitter orange peel has been used in dietary supplements as an aid to fat loss and as an appetite suppressant. Bitter orange contains the tyramine metabolites N-methyltyramine, octopamine and synephrine, substances similar to epinephrine, which acts on the $\alpha_1$-adrenergic receptor to constrict blood vessels and increase blood pressure and heart rate. Other uses include as a remedy to treat heart burn, nasal congestion, treat fungal infections, as a fat burner, and for increasing mental focus and providing energy. The bitter orange peel is used as an appetite stimulant and for dyspepsia. Bitter orange fruit and peel are also used orally for weight loss, increasing lean body mass, body building, improving athletic performance, nasal congestion, allergic rhinitis, and chronic fatigue syndrome (CFS). The bitter orange flower and its oil are used orally for gastrointestinal (GI) disturbances, duodenal ulcers, constipation, regulating blood lipid levels, lowering blood sugar in diabetes, hyperlipidemia, blood purification, functional disorders of liver and gallbladder, stimulation of the heart and circulation, frostbite, as a sedative for sleep disorders, for kidney and bladder diseases, general feebleness, anemia, imbalances of mineral metabolism, impurities of the skin, hair loss, as a tonic, anti-flatulent, and for cancer. Other uses include administration to relieve prolapsed uterus, prolapsed anus or rectum, diarrhea, and blood in the stools. Topically, bitter orange peel is used for inflammation of the eyelid, conjunctiva, and retina. It is also used for retinal hemorrhage and to relieve exhaustion accompanying colds.

In certain embodiments, the composition comprises 1, 3 dimethylethylalanine. Alanine is an alpha-amino acid having a chemical formula of $CH_3Ch(NH)_2COOH$. It is a nonessential amino acid found in foods, and acts as one of the building blocks for proteins.

In certain embodiments, the composition comprises Hordenine. Hordenine is an ingredient of some plants which are used as feed for animals, i.e. in sprouting barley. Hordenine (N,N-dimethyl-4-hydroxyphenylethylamine) is a phenethylamine alkaloid with antibacterial and antibiotic properties. It stimulates the release of norepinephrine in mammals, working as a stimulant. It is produced in nature by several varieties of plants in the family Cactaceae and by some in Acacia. Hordenine has been promoted as a weight loss agent with the claim that it stimulates the central nervous system. It has also been used as a beta agonist and as a metabolic stimulant. Although little research has been done on hordenine, results of some experiments in pharmacological models show that hordenine is an indirectly acting adrenergic drug. In isolated organs and those structures with reduced epinephrine contents, the hordenine-has been shown to have minimal effect. Experiments in intact animals (rats, dogs) show that hordenine has a positive inotropic effect upon the heart, increases systolic and diastolic blood pressure, peripheral blood flow volume, and inhibits gut movements.

In some embodiments, the composition comprises green apple pectin, or fibersol, or other fiber source. Pectin in the plant starting material is part of a very complex structure, which gives shape to the soft non-woody parts of the plant. It is a structural heteropolysaccharide contained in the primary cell walls of terrestrial plants. Pectin is a natural part of human diet, but does not contribute significantly to nutrition as it is a soluble dietary fiber. Green apple pectin has been used to absorb metals, toxins, fats, and to reduce heaviness in the blood. Fibersol is a resistant maltodextrin, or alternatively, a digestion resistant maltodextrin. It is 90% resistant to digestion by the human digestive system. Fibersol is sold as digestion resistant maltodextrin to clearly define that is it resistant to digestion and that it is not a digestible carbohydrate. It is typically supplied in capsules containing natural, bulk producing, soluble dietary fiber derived from fruit and plants. Each capsule provides the benefits of hemicelluloses (gum and pectin) and polysaccharides which are important for maintaining the proper pace and bulk required for healthy digestive function.

In some embodiments, the composition comprises N-acetyl L-cysteine (NAC). It is a pharmaceutical drug and nutritional supplement which has been used primarily as a mucolytic agent (expectorant), and in the management of paracetamol (acetaminophen) overdose. Other uses include sulfate repletion in conditions, such as autism, where cysteine and related sulfur amino acids may be depleted. NAC is a derivative of cysteine in which an acetyl group is attached to the nitrogen atom. It is sold as a dietary supplement commonly claiming antioxidant and liver protecting effects (detoxifying). It is used as a cough medicine because it breaks disulfide bonds in mucus and liquefies it, making it easier to cough up. It is also this action of breaking disulfide bonds that makes it useful in thinning the abnormally thick mucus in Cystic Fibrosis patients.

In some embodiments, the composition comprises vinpocetine. Vinpocetine is a semi-synthetic derivative alkaloid of vincamine, an extract from the periwinkle plant. Vinpocetine has been shown to be a cerebral metabolic enhancer and a selective cerebral vasodilator. Vinpocetine is reported to have cerebral blood flow enhancing and neuroprotective effects, and has been used for the treatment of cerebrovascular disorders and age-related memory impairment. Vinpocetine is marketed as a supplement for vasodilation and as a nootropic for the improvement of memory. Vinpocetine may help support brain functions such as concentration and memory by activating cerebral metabolism. Vinpocetine has also been identified as a potent anti-inflammatory agent that might have a potential role in the treatment of Parkinson's disease and Alzheimer's disease.

In some embodiments, the composition comprises tyrosine. Tyrosine (4-hydroxyphenylalanine) is a nonessential amino acid the body makes from another amino acid called phenylalanine. Tyrosine is found in soy products, chicken, turkey, fish, peanuts, almonds, avocados, bananas, milk, cheese, yogurt, cottage cheese, lima beans, pumpkin seeds, and sesame seeds. It is a building block for several important neurotransmitters, including epinephrine, norepinephrine, and dopamine. Tyrosine also helps produce melanin (the pigment responsible for hair and skin color) and helps in the function of organs responsible for making and regulating hormones, including the adrenal, thyroid, and pituitary glands. It is involved in the structure of almost every protein, in the body and in the production of the stress hormones epinephrine and norepinephrine. A number of studies have found tyrosine to be useful during conditions of stress, cold, fatigue, loss of a loved one such as in death or divorce, prolonged work and sleep deprivation, with reductions in stress hormone levels, reductions in stress-induced weight loss seen in animal trials, and improvements in cognitive and physical performance seen in human trials.

In some embodiments, the composition comprises quercetin. Quercetin is a type of plant-based chemical, or phytochemical, known as a flavonoid found in apples, onions, teas, red wines, and many other foods. Flavonoids such as quercetin are antioxidants which scavenge free radicals, the substances which damage cell membranes, tamper with DNA, and even cause cell death. Antioxidants can neutralize free radicals and may reduce or even help prevent some of the damage they cause. They also help keep LDL cholesterol from being damaged. Quercetin may have anti-inflammatory properties. It has been promoted as being effective against a wide variety of diseases, including cancer.

In some embodiments, the composition comprises piracetam. Piracetam chemical name 2-oxo-1-pyrrolidine acetamide, is a nootropic drug. Nootropics are known commonly as cognitive enhancers, improving cognitive functions of the brain such as memory, attention and intelligence. Piracetam improves brain function and stimulates the central nervous system without any toxicity or addictive properties.

In some embodiments, the composition comprises B-vitamin mix. B-vitamins are a group of water-soluble vitamins that play important roles in cell metabolism. While originally thought to be a single vitamin, referred to as vitamin B, there exists eight chemically distinct B vitamins, including Vitamin $B_1$ (thiamine), Vitamin $B_2$ (riboflavin), Vitamin $B_3$ (niacin or niacinamide), Vitamin $B_5$ (pantothenic acid), Vitamin $B_6$ (pyridoxine, pyridoxal, pyridoxamine, or pyridoxine hydrochloride), Vitamin $B_7$ (biotin), Vitamin $B_9$ (folic acid), Vitamin $B_{12}$ (various cobalamins, commonly cyanocobalamin in vitamin supplements). B vitamins are essential for growth, development, and a variety of other bodily functions. They play a major role in the activities of enzymes, proteins that regulate chemical reactions in the body, which are important in turning food into energy and other needed substances. The B vitamins are thought to be necessary to support and increase the rate of metabolism, maintain healthy skin and muscle tone, enhance immune and nervous system function, promote cell growth and division, including that of the red blood cells that help prevent anemia, and reduce the risk of pancreatic cancer when consumed in food, but not when ingested in vitamin tablet form.

In some embodiments, the composition comprises an electrolyte mix. Electrolyte refers to salts, specifically ions, which are used by the body's cells (especially nerve, heart, muscle) to maintain voltages across their cell membranes and to carry electrical impulses (nerve impulses, muscle contractions) across themselves and to other cells. One or more of the major electrolytes found in the body may be included in the mix, such as: sodium ($Na^+$), potassium ($K^+$), chloride ($Cl^-$), calcium ($Ca^{2+}$), magnesium ($Mg^{2+}$), bicarbonate ($HCO_3^-$), phosphate ($PO_4^{2-}$), and sulfate ($SO_4^{2-}$). The electrolyte mix may include, for example, calcium glycerol phosphate, magnesium glycerol phosphate, potassium glycerol phosphate, or combinations thereof. Other electrolytes known to one of skill in the art may be used as well.

In some embodiments, the composition comprises dimethylethanolamine (DMAE). DMAE, also known as N,N-dimethyl-2-aminoethanol, beta-dimethylaminoethyl alcohol, beta-hydroxyethyldimethylamine and deanol, is an organic compound. It is a choline molecule that has been used to improve memory and concentration. Some studies have shown that an increase in vigilance and alertness resulted following administration of DMAE, vitamins, and minerals. While long term studies have not been undertaken, nutritional uses for the molecule include boosting immunity, energy, anti-aging effects, weight loss, and aggression.

In some embodiments, the composition comprises xylitol. Xylitol is an organic compound with the formula $(CHOH)_3(CH_2OH)_2$. Xylitol is a naturally occurring sugar substitute. It is a sugar alcohol sweetener found in the fibers of many fruits and vegetables, including various berries, corn husks, oats, and mushrooms. Xylitol differs from other sweeteners such as sorbitol, fructose and glucose in that the Xylitol molecule contains five carbons instead of six.

In some embodiments, the composition comprises potassium bicarbonate. Also known as potassium hydrogen carbonate or potassium acid carbonate, potassium bicarbonate, $KHCO_3$, has been used as a dietary supplement as a source of potassium and as an antacid. Accordingly, the potassium bicarbonate may provide a source of minerals. In some embodiments, the composition may therefore include one or more dietary minerals, i.e. an inorganic element that is essential for human nutrition or promote certain physiological functions, including but not limited to calcium, phosphorous, selenium, magnesium, potassium, sodium, zinc, and iodine. The dietary mineral may be provided individually or in combination such as a salt containing the mineral element and another ion.

In some embodiments, the composition comprises, in combination, one or more ingredients at for example, concentrations of 100 mg to 1500 mg which act as cognitive enhancers (i.e. substances that improve mental functions such as but not limited to cognition, memory, intelligence, motivation, attention, or concentration), neurostimulants, or combinations thereof. Such ingredients include, but are not limited to, one or more of betaphenyethylamine, sida cordifolia, Ma Huang, ephedra, alkaloids ephedrine, C-AMP-adenosine cyclic 3,5-monophosphate, adrafinil, olmifon, synephrine HCl, methyl synephrine, theobromide, theobromine, evodiamine, octopamine, 1,3 dimethylamylamine, (geranamine, or 1,3 dimethylpentylamine), schisandra chemensis, citrus sinensis, paulinia cupana, adhatoda vasica, visnea mocanera, vitis vinfera, cocoa bean extract, 99% methylxanitines, evodia rutaecarpa 99% evodiamine, Rauwolscine canescens, raspberry ketones, tyramine, sulbutiamine, methyl B-12, proactive B-vitamins, Phenyl ethyl amine (PEA), amino acid precursors, dendrobium nobile (DEN, herb and member of the family Orchidaceae), dihydromyricetin (DHM).

In some embodiments, the composition comprises one or more ingredients at concentrations of 100 mg to 1000 mg that act as mental focusing agents. Such ingredients include, but are not limited to, one or more of oxytropis falcate, caffeine based or derived stimulants such as yerba mate, chocoamine, theobromine, bromide, guranna, green or black teas, kola nut.

In some embodiments, the composition comprises one or more amino acids other than described above, particularly those that act as cognitive enhances, improve mental focus, and act as balance enhancers. Such amino acids include, but are not limited to, one or more of L-carnitine in any form, serine in any form, choline in any form, alpha glycerol phosphocholine, and glutamine in any form.

In some embodiments, the composition comprises herbal substances or compositions such as Milk thistle. Milk thistle, a thistle of the genus *Silybum*, contains active an flavanoid-lignan constituent called silymarin. Such constituent is known to act as an anti-oxidant, and has shown to have liver protective and regenerative properties.

In some embodiments, the composition comprises stabilizers, which may include preservatives such as but not limited to benzaldehydes, PEG (poly ethyl glycohol), or carboxylic acid.

The composition can be formulated in any conventional manner. The actual composition may, therefore, be formulated based on the route of administration chosen. Illustrative administration routes include, but are not limited to, oral (such as but not limited to liquid), parenteral (for example, intravenous, intraarterial, subcutaneous, rectal, intramuscular, intraorbital, intracapsular, intraspinal, intraperitoneal, intrasternal), topical (for example nasal, transdermal, intraocular), intravesical, intrathecal, enteral, pulmonary, intralymphatic, intracavital, vaginal, transurethral, intradermal, aural, intramammary, buccal, orthotopic, intrathecal, intralesional, percutaneous, endoscopical, transmucosal, sublingual, and intestinal administration. Accordingly, illustrative examples of the composition form may include but are not limited to tablets, capsules, caplets, pills, gel caps, troches, dispersions, suspensions, liquids, solutions, syrups, or dissolvable strips for placement in the mouth, granules, beads, transdermal patches, gels, powders, pellets, magmas, lozenges, creams, pastes, plasters, lotions, discs, suppositories, liquid sprays for nasal or oral administration, dry powders, dry powder or aerosolized formulations for inhalation, compositions and formulations for intravesical administration.

Example 1: Composition for Improving Cognitive Ability and/or Reducing Blood Alcohol Levels in an Individual Impaired or Suspected of being Impaired by an Alcoholic Substance

| Compound | Percentage of Overall Composition (by weight or volume) |
| --- | --- |
| At least one Neurostimulants/Metabolic Stimulants | 40% |
| At least one Cognitive enhancers | 20% |
| At least one Amino acids | 20% |

-continued

| Compound | Percentage of Overall Composition (by weight or volume) |
|---|---|
| At least one Vitamins and minerals | 10% |
| At least one Antioxidants | 5% |
| At least one Stabilizers/Preservatives/other | 5% |

In an alternative embodiment, the composition for reducing blood alcohol levels, in an individual impaired by an alcoholic substance in accordance with the present invention may comprise about 8 parts by weight of at least one neurostimulant, about 4 parts by weight of at least one cognitive enhancer, about 4 parts by weight of at least one amino acid, about 2 parts by weight of at least one vitamin and/or mineral, about 1 part by weight of at least one antioxidant, and about 1 part by weight of at least one stabilizer.

Example 2: Composition for Improving Cognitive Ability and/or Reducing Blood Alcohol Levels in an Individual Impaired or Suspected of being Impaired by an Alcoholic Substance

| Compound | Amount |
|---|---|
| Cognitive Enhancers | 1.0 mg-1500 mg |
| Neurostimulants and/or Metabolic stimulants | 1.0 mg-1500 mg |
| Amino acids | 1.0 mg-1000 mg |
| Vitamins | 1.0 mg-500 mg |
| Electrolytes | 1.0 mg-500 mg |
| Minerals | 1.0 mg-500 mg |
| Dietary fiber | 1.0 mg-2000 mg |
| Preservatives | 1.0 mg-1000 mg |
| Anti-oxidants | 1.00 mg-1000 mg |

Example 3: Oral (Liquid) Composition

| Compound | Amount |
|---|---|
| Bitter orange | 15-1000 mg |
| 1,3 dimethylethylalanine | 15-1000 mg |
| Hordenine | 15-1000 mg |
| green apple pectin, or fibersol, or other fiber source | 500-2000 mg |
| N-acetyl cysteine (NAC) | 250-1000 mg |
| Vinpocetine | 10-100 mg |
| Tyrosine | 250-1000 mg |
| Quercetin | 250-1000 mg |
| Piracetam | 250-1000 mg |
| B-vitamin mix: mixture of one or more of Vitamin $B_1$ (thiamine), Vitamin $B_2$ (riboflavin), Vitamin $B_3$ (niacin or niacinamide), Vitamin $B_5$ (pantothenic acid), Vitamin $B_6$ (pyridoxine, pyridoxal, or pyridoxamine, or pyridoxine hydrochloride), Vitamin $B_7$ (biotin), Vitamin $B_9$ (folic acid), Vitamin $B_{12}$ (various cobalamins). | 100-500 mg |
| Electrolyte mix: mixture of one or more of sodium ($Na^+$), potassium ($K^+$), chloride ($Cl^-$), calcium ($Ca^{2+}$), magnesium ($Mg^{2+}$), bicarbonate ($HCO_3^-$), phosphate ($PO_4^{2-}$), and sulfate ($SO_4^{2-}$). | 50-500 mg |
| Dimethylethanolamine (DMAE) | 50-500 mg |
| Xylitol | As needed |
| Potassium bicarbonate | As needed |
| Flavoring | As needed |

Example 4: Oral (Liquid) Composition

| Compound | Amount |
|---|---|
| Bitter orange | 50 mg |
| 1,3 dimethylethylalanine | 30 mg |
| Hordenine | 25 mg |
| green apple pectin or fibersol, or other fiber source | 1 g |
| N-acetyl cysteine (NAC) | 250 g |
| Vinpocetine | 10-20 mg |
| Tyrosine | 250 mg |
| Quercetin | 500 mg |
| Piracetam | 500 mg |
| B-vitamin mix: mixture of one or more of Vitamin $B_1$ Vitamin $B_2$, Vitamin $B_5$, Vitamin $B_6$, Vitamin $B_{12}$. | 250 mg |
| Electrolyte mix | 250 mg |
| Dimethylethanolamine (DMAE) | 100 mg |
| Xylitol | As needed |
| Potassium bicarbonate | As needed |
| Lemon-lime or tropical punch | As needed |

Example 5: Oral (Liquid) Composition

| Compound | Amount |
|---|---|
| Bitter orange | 50 mg |
| 1,3 dimethylethylalanine | 30 mg |
| Hordenine | 25 mg |
| green apple pectin | 1 g |
| N-acetyl cysteine (NAC) | 250 g |
| Vinpocetine | 20 mg |
| N-acetyl-tyrosine | 300 mg |
| Quercetin | 500 mg |
| Piracetam | 500 mg |
| Vitamin $B_1$ | 50 mg |
| Vitamin $B_2$ | 50 mg |
| Vitamin $B_3$ | 200 mg |
| Vitamin $B_5$ | 50 mg |
| Vitamin $B_6$ | 200 mg |
| Vitamin $B_{12}$ | 1000 mg |
| N-acetyl cysteine | 250 mg |
| Milk Thistle | 300 mg |
| Calcium glycerol phosphate | 200 mg |
| Magnesium glycerol phosphate | 100 mg |
| Potassium glycerol phosphate | 50 mg |
| Dimethylethanolamine (DMAE) | 100 mg |
| Xylitol | As needed |
| Potassium bicarbonate | As needed |
| Flavoring agent | As needed |

Methods for Testing of Intoxicated Individuals and Administration of Composition:

The Example 3 composition was tested in order to observe and record the effects the liquid composition has in relation to individuals who are intoxicated from drinking beverages containing alcohol. Five individuals, four men and one woman, were used in the test population. Each of the individuals was allowed to consume beverages containing alcohol, such as beer or liquor, over a specific time such that their blood alcohol levels were over the legal driving limits of 0.08. Since a person found driving with a blood-alcohol concentration (BAC) level exceeding the legal limit can be arrested and charged with the offense of driving under the influence (DUI), this was the value chosen as a comparison point. However, the compositions in accordance with the instant invention can be effective in individuals who have lower BAC levels as well. A standard breathalyzer machine, such as the Intoxilyzer 8000 (CMI, Inc. Owensboro, Ky.) or portable breathalyzer machines, such as Alco-Hawk (Q3 Asset Acquisition, LLC, Independence, Iowa)

which measures the blood-alcohol concentration was used to determine the levels of alcohol in each of the individual's system. In addition to measuring the blood alcohol level, each of the individuals was tested to examine their facultative and physical capabilities in order to determine effects and improvement to the individual's cognitive capabilities or behaviors. Such testing is similar to field sobriety tests performed by police offers in the field when the officers encounter drivers they believe exhibit characteristics of drunk driving, and/or asked to comment about their state of drunkenness. Table 1 below summarizes the results for all individuals that participated in the experiment.

TABLE 1

Summary: Experimental Results:

| Subject | Pre-Drink BAC Level | Post Drink Behavior | Post-Administration of Composition: BAC Levels | Post-Administration of Composition: Behavior | Time Period of BAC Determination Post Administration of Composition |
|---|---|---|---|---|---|
| 1. Male | 0.18 | Feeling of being drunk or "buzzed"; most likely would have failed a field sobriety test | 0.03 | Appeared to exhibit normal behavior; increased cognitive capabilities compared to-impaired state | 16 minutes (second post drink test of 0.03 at 45 minutes) |
| 2. Male | 0.21 | Feeling of being drunk; most likely would have failed a field sobriety test | 0.05 | Appeared to exhibit normal behavior; increased cognitive capabilities compared to-impaired state | 16 minutes (second post drink test result of 0.05 at 34 minutes) |
| 3. Male | 0.10 | Most likely would have failed a field sobriety test | 0.04 | Appeared to exhibit normal behavior; increased cognitive capabilities compared to-impaired state | 16 minutes |
| 4. Female | 0.17 | Most likely would have failed a field sobriety test | 0.05 | Appeared to exhibit normal behavior; increased cognitive capabilities compared to-impaired state | 15 minutes (second post drink test result of 0.05 at 34 minutes) |
| 5. Male | 0.14 | Most likely would have failed a field sobriety test | 0.01 | Appeared to exhibit normal behavior; increased cognitive capabilities compared to-impaired state | 15 minutes |

Example 1: Subject 1

Subject Number 1 was allowed to drink beverages containing alcohol. An initial alcohol drunkenness assessment was carried out, consisting of both subjective and objective testing means. A standard portable breathalyzer machine was used to determine the levels of alcohol in his system. In addition to the breathalyzer test, Subject Number 1 was visually examined, asked to perform a variety of tests in order to subjectively determine the level of alcohol impairment or intoxication by evaluating his/her coordination, cognitive abilities, and capacity to follow instructions, and/or asked to describe state of drunkenness. After drinking the alcoholic beverages, the initial breathalyzer test indicated a BAC of 0.18. The subject described himself as feeling drunk. After an initial assessment was determined, Subject Number 1 was given an oral dosage of the composition in accordance with Example Number 3. After a period of 16 minutes post administration of the composition, Subject Number 1 was given a second evaluation to determine the level of alcohol impairment. As before, the assessment consisted of a determination of the amount of alcohol in the blood through the use of a standard breathalyzer machine, and a subjective test. Subject Number 1 had a post-drink breathalyzer test BAC of 0.03 and exhibited normal behavior. A third measurement of BAC levels was determined for Subject Number 1. After a period of 45 minutes after drinking the composition, BAC was measured at 0.03.

Example 2: Subject 2

Subject Number 2 was allowed to drink beverages containing alcohol. An initial alcohol drunkenness assessment was carried out, consisting of both subjective and objective testing means. A standard portable breathalyzer machine was used to determine the levels of alcohol in his system. In addition to the breathalyzer test, Subject Number 2 was visually examined, asked to perform a variety of tests in order to subjectively determine the level of alcohol impairment or intoxication by evaluating his coordination, cognitive abilities, and capacity to follow instructions, and/or asked to describe state of drunkenness. After drinking the alcoholic beverages, the initial breathalyzer test indicated a BAC of 0.21. The subject described himself as feeling drunk. After an initial assessment was determined, Subject Number 2 was given an oral dosage of the composition in accordance with Example Number 3. After a period of 16 minutes post administration of the composition, Subject Number 2 was given a second evaluation to determine the level of alcohol impairment. As before, the assessment consisted of a determination of the amount of alcohol in the blood through the use of a standard breathalyzer machine, and a subjective test. Subject Number 2 had a post-drink breathalyzer test BAC of 0.05 and exhibited normal behavior. A third measurement of BAC levels was determined for Subject Number 2. After a period of 34 minutes after drinking the composition, BAC was measured at 0.05.

Example 3: Subject 3

Subject Number 3 was allowed to drink beverages containing alcohol. An initial alcohol drunkenness assessment was carried out, consisting of both subjective and objective testing means. A standard portable breathalyzer machine was used to determine the levels of alcohol in his system. In addition to the breathalyzer test, Subject Number 3 was visually examined, asked to perform a variety of tests in order to subjectively determine the level of alcohol impairment or intoxication by evaluating his coordination, cognitive abilities, and capacity to follow instructions, and/or asked to describe state of drunkenness. After drinking the alcoholic beverages, the initial breathalyzer test indicated a BAC of 0.10. The subject described himself as feeling drunk. After an initial assessment was determined, Subject Number 3 was given an oral dosage of the composition in accordance with Example Number 3. After a period of 15 minutes post administration of the composition, Subject Number 3 was given a second evaluation to determine the level of alcohol impairment. As before, the assessment consisted of a determination of the amount of alcohol in the blood through the use of a standard breathalyzer machine, and a subjective test. Subject Number 3 had a post-drink breathalyzer test BAC of 0.04 and exhibited normal behavior. A third measurement of BAC levels was not determined for Subject Number 3.

Example 4: Subject 4

Subject Number 4 was allowed to drink beverages containing alcohol. An initial alcohol drunkenness assessment was carried out, consisting of both subjective and objective testing means. A standard portable breathalyzer machine was used to determine the levels of alcohol in her system. In addition to the breathalyzer test, Subject Number 4 was visually examined, asked to perform a variety of tests in order to subjectively determine the level of alcohol impairment or intoxication by evaluating her coordination, cognitive abilities, and capacity to follow instructions, and/or asked to describe state of drunkenness. After drinking the alcoholic beverages, the initial breathalyzer test indicated a BAC of 0.17. The subject described herself as feeling drunk. After an initial assessment was determined, Subject Number 4 was given an oral dosage of the composition in accordance with Example Number 3. After a period of 15 minutes post administration of the composition, Subject Number 4 was given a second evaluation to determine the level of alcohol impairment. As before, the assessment consisted of a determination of the amount of alcohol in the blood through the use of a standard breathalyzer machine, and a subjective test. Subject Number 4 had a post-drink breathalyzer test BAC of 0.05 and exhibited normal behavior. A third measurement of BAC levels was determined for Subject Number 4. After a period of 34 minutes after drinking the composition, BAC was measured at 0.05.

Example 5: Subject 5

Subject Number 5 was allowed to drink beverages containing alcohol. An initial alcohol drunkenness assessment was carried out, consisting of both subjective and objective testing means. A standard portable breathalyzer machine was used to determine the levels of alcohol in his system. In addition to the breathalyzer test, Subject Number 5 was visually examined, asked to perform a variety of tests in order to subjectively determine the level of alcohol impairment or intoxication by evaluating his coordination, cognitive abilities, and capacity to follow instructions, and/or asked to describe state of drunkenness. After drinking the alcoholic beverages, the initial breathalyzer test indicated a BAC of 0.14. The subject described himself as feeling drunk. After an initial assessment was determined, Subject Number 5 was given an oral dosage of the composition in accordance with Example Number 3. After a period of 15 minutes post administration of the composition, Subject Number 5 was given a second evaluation to determine the level of alcohol impairment. As before, the assessment consisted of a determination of the amount of alcohol in the blood through the use of a standard breathalyzer machine, and a subjective test. Subject Number 5 had a post-drink breathalyzer test BAC of 0.01 and exhibited normal behavior. A third measurement of BAC levels was not determined for Subject Number 5.

While the present invention is susceptible of embodiment in various forms, there is shown and will hereinafter be described a presently preferred, albeit not limiting, embodiment with the understanding that the present disclosure is to be considered an exemplification of the present invention and is not intended to limit the invention to the specific embodiments illustrated.

All patents and publications mentioned in this specification are indicative of the levels of those skilled in the art to which the invention pertains. All patents and publications are herein incorporated by reference to the same extent as if each individual publication, was specifically and individually indicated to be incorporated by reference.

It is to be understood that while a certain form of the invention is illustrated, it is not to be limited to the specific form or arrangement herein described and shown. It will be apparent to those skilled in the art that various changes may be made without departing from the scope of the invention and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary and are not intended as limitations on the scope.

Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A composition for improving cognitive performance and reducing blood alcohol concentrations (BAC) in an individual suspected of being impaired by an alcoholic substance comprising, a first cognitive enhancer being vinpocetine, at least one second cognitive enhancer, at least one neurostimulant, at least one amino acid, at least one B-vitamin, at least one electrolyte, at least one anti-oxidant, an effective amount of bitter orange, an effective amount of 1,3-dimethylamylamine, an effective amount of hornedine, an effective amount of vinpocetine, an effective amount of tyrosine, and effective amount of quercetin, an effective amount of piracetam, an effective amount of dimethylethanolamine (DMAE), an effective amount of caffeine, an effective amount of fiber, an effective amount of N-acetyl cysteine (NAC), and an effective amount of at least one electrolyte, said composition resulting in clearance of alcohol from an individual at a faster rate than achieved under normal physiological time periods.

2. The composition for improving cognitive performance and reducing blood alcohol concentrations (BAC) in an individual suspected of being impaired by an alcoholic substance according to claim 1 further including at least one preservative, and at least one dietary mineral.

3. The composition for improving cognitive performance and reducing blood alcohol concentrations (BAC) in an individual suspected of being impaired by an alcoholic substance according to claim 1 wherein the said second cognitive enhancer is an herbal cognitive enhancer.

4. The composition for improving cognitive performance and reducing blood alcohol concentrations (BAC) in an individual suspected of being impaired by an alcoholic substance according to claim 1 wherein the at least one B-vitamin includes Vitamin $B_1$, Vitamin $B_2$, Vitamin $B_3$, Vitamin $B_5$, Vitamin $B_6$, Vitamin $B_{12}$, or combinations thereof.

5. The composition for improving cognitive performance and reducing blood alcohol concentrations (BAC) in an individual suspected of being impaired by an alcoholic substance according to claim 1 wherein said composition is in the form of a tablet, capsule, caplet, pill, gel cap, dry powder, liquid, or suspension.

6. A composition for improving cognitive performance and reducing blood alcohol concentrations (BAC) in an individual suspected of being impaired by an alcoholic substance, wherein the composition comprises:
an effective amount of bitter orange extract;
an effective amount of 1,3-dimethylamylamine;
an effective amount of hornedine; and
an effective amount of caffeine;
whereby administration of said compound results in the clearance of alcohol from the body at a faster rate than clearance associated under normal physiological time periods.

7. The composition for improving cognitive performance and reducing blood alcohol concentrations (BAC) in an individual suspected of being impaired by an alcoholic substance according to claim 6, further comprising an effective amount of vinpocetine.

8. The composition for improving cognitive performance and reducing blood alcohol concentrations (BAC) in an individual suspected of being impaired by an alcoholic substance according to claim 6, further comprising an effective amount of a quercetin.

9. The composition for improving cognitive performance and reducing blood alcohol concentrations (BAC) in an individual suspected of being impaired by an alcoholic substance according to claim 6, further comprising an effective amount of at least one B-vitamin.

10. The composition for improving cognitive performance and reducing blood alcohol concentrations (BAC) in an individual suspected of being impaired by an alcoholic substance according to claim 6, further comprising an effective amount of tyrosine.

11. The composition for improving cognitive performance and reducing blood alcohol concentrations (BAC) in an individual suspected of being impaired by an alcoholic substance according to claim 6, further comprising an effective amount of at least one electrolyte.

12. The composition for improving cognitive performance and reducing blood alcohol concentrations (BAC) in an individual suspected of being impaired by an alcoholic substance according to claim 6, further comprising an effective amount of N-acetyl cysteine (NAC).

13. The composition for improving cognitive performance and reducing blood alcohol concentrations (BAC) in an individual suspected of being impaired by an alcoholic substance according to claim 6, further comprising an effective amount of piracetam.

14. The composition for improving cognitive performance and reducing blood alcohol concentrations (BAC) in an individual suspected of being impaired by an alcoholic substance according to claim 6, further comprising an effective amount of dimethylethanolamine (DMAE).

* * * * *

UNITED STATES PATENT AND TRADEMARK OFFICE
CERTIFICATE OF CORRECTION

PATENT NO. : 10,028,991 B2
APPLICATION NO. : 14/933286
DATED : July 24, 2018
INVENTOR(S) : Gregory Blackman Page 1 of 1

It is certified that error appears in the above-identified patent and that said Letters Patent is hereby corrected as shown below:

In the Claims

Column 19, Line 21, Claim 1, delete "hornedine," and insert -- hordenine, --

Column 20, Line 7, Claim 6, delete "hornedine;" and insert -- hordenine; --

Signed and Sealed this
Thirtieth Day of October, 2018

Andrei Iancu
*Director of the United States Patent and Trademark Office*